(12) United States Patent
Kim et al.

(10) Patent No.: US 9,409,816 B2
(45) Date of Patent: Aug. 9, 2016

(54) HIGH STRENGTH AND AESTHETIC LITHIUM DISILICATE CRYSTALLINE GLASS-CERAMICS CONTAINING CRISTOBALITE CRYSTAL AND PREPARATION METHOD THEREOF

(71) Applicant: HASS CO., LTD., Gangneung-si (KR)

(72) Inventors: Yong su Kim, Gangneung-si (KR); Hyun jun Jeon, Busan (KR); Hyung bong Lim, Ansan-si (KR); Kyung sik Oh, Incheon (KR); Sung ho Ha, Ansan-si (KR); Cheol young Kim, Seoul (KR); Joon hyung Kim, Ansan-si (KR); Young pyo Hong, Gangneung-si (KR)

(73) Assignee: HASS CO., LTD., Gangneung-Si (KR)

( * ) Notice: Subject to any disclaimer, the term of this patent is extended or adjusted under 35 U.S.C. 154(b) by 0 days.

(21) Appl. No.: 14/539,965

(22) Filed: Nov. 12, 2014

(65) Prior Publication Data

US 2016/0060159 A1 Mar. 3, 2016

(30) Foreign Application Priority Data

Aug. 29, 2014 (KR) ........................ 10-2014-0113633

(51) Int. Cl.
| | |
|---|---|
| *C03C 10/14* | (2006.01) |
| *C03C 10/00* | (2006.01) |
| *C03C 3/097* | (2006.01) |
| *C03B 32/02* | (2006.01) |
| *A61C 5/10* | (2006.01) |
| *A61K 6/02* | (2006.01) |
| *C03B 19/02* | (2006.01) |

(Continued)

(52) U.S. Cl.
CPC ............... *C03C 10/0027* (2013.01); *A61C 5/10* (2013.01); *A61K 6/024* (2013.01); *A61K 6/0273* (2013.01); *A61K 6/0612* (2013.01); *C03B 19/025* (2013.01); *C03B 32/02* (2013.01); *C03C 3/097* (2013.01); *C03B 2201/28* (2013.01); *C03B 2201/32* (2013.01); *C03B 2201/40* (2013.01); *C03B 2201/50* (2013.01); *C03B 2201/54* (2013.01); *C03C 2204/00* (2013.01)

(58) Field of Classification Search
CPC .................................................. C03C 10/0027
USPC ....................................................... 501/5, 6, 7
See application file for complete search history.

(56) References Cited

U.S. PATENT DOCUMENTS

| | | |
|---|---|---|
| 3,804,608 A | 4/1974 | Gaskell et al. |
| 4,189,325 A | 2/1980 | Barrett et al. |
| 4,515,634 A | 5/1985 | Wu et al. |

(Continued)

FOREIGN PATENT DOCUMENTS

| | | |
|---|---|---|
| EP | 1253116 | 10/2002 |
| EP | 1005841 | 2/2005 |

(Continued)

*Primary Examiner* — Noah Wiese
(74) *Attorney, Agent, or Firm* — H.C. Park & Associates, PLC

(57) ABSTRACT

Provided is lithium disilicate crystalline glass containing cristobalite crystal phase for high strength and aesthetic traits and its manufacturing process thereof. Exemplary embodiments of the present invention provide the high strength and aesthetic lithium disilicate crystalline glass, one kind of dental restoration materials, and its manufacturing method which induces the growth of the different crystal phase, cristobalite, from glass with lithium disilicate crystal.

10 Claims, 4 Drawing Sheets

(51) Int. Cl.
  *A61K 6/027* (2006.01)
  *A61K 6/06* (2006.01)

(56) References Cited

U.S. PATENT DOCUMENTS

| | | | |
|---|---|---|---|
| 5,219,799 A | 6/1993 | Beall et al. | |
| 5,968,856 A * | 10/1999 | Schweiger | C03C 10/0009 |
| | | | 106/35 |
| 6,342,458 B1 | 1/2002 | Schweiger et al. | |
| 6,372,319 B1 | 4/2002 | Abe et al. | |
| 6,375,729 B1 | 4/2002 | Brodkin et al. | |
| 6,420,288 B2 | 7/2002 | Schweiger et al. | |
| 6,455,451 B1 * | 9/2002 | Brodkin | A61K 6/033 |
| | | | 106/35 |
| 6,495,480 B1 * | 12/2002 | Goto | C03C 10/0027 |
| | | | 428/846.9 |
| 6,514,893 B1 | 2/2003 | Schweiger et al. | |
| 6,517,623 B1 | 2/2003 | Brodkin et al. | |
| 6,606,884 B2 | 8/2003 | Schweiger et al. | |
| 6,802,894 B2 * | 10/2004 | Brodkin | C03B 19/06 |
| | | | 106/35 |
| 6,818,573 B2 * | 11/2004 | Petticrew | A61C 13/20 |
| | | | 106/35 |

FOREIGN PATENT DOCUMENTS

| | | |
|---|---|---|
| EP | 1534169 | 3/2006 |
| JP | 2000086289 | 3/2000 |
| JP | 2011225441 | 11/2011 |
| JP | 2012-250911 | 12/2012 |
| KR | 1020120073710 | 7/2012 |
| KR | 10-1262121 | 5/2013 |

\* cited by examiner

| Thermal expansion coefficient | | | | | | |
|---|---|---|---|---|---|---|
| | Cristobalite | 65 wt.% $SiO_2$ | 70 wt.% $SiO_2$ | 72 wt.% $SiO_2$ | 75 wt.% $SiO_2$ | 77 wt.% $SiO_2$ |
| $\alpha_{\text{rt-600}}$ ($\times 10^{-6}/°C$) | 10.9 | 10.8 | 10.5 | 9.9 | 9.5 | 9.3 |

HIGH STRENGTH AND AESTHETIC LITHIUM DISILICATE CRYSTALLINE GLASS-CERAMICS CONTAINING CRISTOBALITE CRYSTAL AND PREPARATION METHOD THEREOF

CROSS-REFERENCE TO RELATED APPLICATION

This application claims priority from and the benefit under 35 U.S.C. §119(a) of Korean Patent Application No. 10-2014-0113633, filed on Aug. 29, 2014, which is incorporated herein by reference as if fully set forth herein.

BACKGROUND

1. Field

The present disclosure relates to high strength and aesthetic lithium disilicate crystalline glass-ceramics including cristobalite crystal and a preparation method thereof. The preparation method relates to a preparation of the high strength and aesthetic lithium disilicate crystalline glass-ceramics, dental restoration materials, and manufacturing methods which induce the growth of crystal phases or structures in a glass matrix with lithium disilicate crystal.

2. Discussion of the Background

With increased interest in appearance from economic development and increased income, the aesthetic aspect of prosthetic dental materials gains high attention. This leads to the introduction to different kinds of prosthetic restoration materials with aesthetic functions, and also to the development of various non-metal restoration materials.

Crown materials refer to prosthetic materials for restoration of the damaged teeth surfaces relevant to dentin and enamel. They are classified into inlay, onlay, veneer, and crown depending on the areas to be applied. Since they are applied to the outmost surfaces or teeth, not only aesthetic traits are highly required, but also high strength is demanded to endure chipping and/or wear against opposing dentition. Materials previously developed for crowns are leucite glass ceramics, reinforced porcelain, and fluorapatite ($Ca_5(PO_4)_3F$) crystalline glass. Though they have high aesthetic traits, they are subject to fracture due to low flexural strength around 80 to 120 MPa. Therefore, various crown materials with high strength are being developed.

Lithium disilicate crystalline glass was introduced by Marcus P. Borom and Anna M. Turkalo (The Pacific Coast Regional Meeting, The American Ceramic Society, San Francisco, Calif., Oct. 31, 1973 (Glass division, No. 3-G-73P)) in 1973. They studied the formation of various crystal nuclei, and the different crystal phases and strength according to various heat treatment conditions for nuclei growth using glasses from $Li_2O$—$Al_2O_3$—$SiO_2$—$Li_2O$—$K_2O$—$B_2O_3$—$P_2O_5$. The high-temperature lithium disilicate crystal formed from low-temperature lithium meta-silicate showed its strength at 30-35 kps. It was due to the residual stress caused by the different thermal expansion coefficient of different phases, that is, reinforced glass, mother glass, $Li_2SiO_5$, and $Li_2SiO_3$ crystals.

High strength crystalline glass for dentistry (monolithic dental crown) using crystalline glass including lithium disilicate crystal has been provided. Although this crystalline glass has high aesthetic traits, the mechanical strength of monolithic crown manufactured by such method is low around 350 MPa, which is not adequate for posterior or bridges exposed to high stress. Therefore, various studies are under way to increase the strength of these aesthetic materials.

SUMMARY

An exemplary embodiment of the present invention provides dental lithium disilicate glass-ceramics containing cristobalite crystal with high strength as well as aesthetic traits.

An exemplary embodiment of the present invention provides a manufacturing method of preparing dental lithium disilicate glass-ceramics containing cristobalite crystal with high strength as well as aesthetic traits.

An exemplary embodiment of the present invention provides a lithium silicate glass composition for crystallizing to a lithium disilicate glass-ceramic having a cristobalite crystal phase, the lithium silicate glass composition including: a glass component including 11-13 wt % $Li_2O$, 70.0-77.0 wt % $SiO_2$, 2-3 wt % $P_2O_5$ as a nuclei formation agent, 2-5 wt % $Al_2O_3$ to increase glass transition temperature, softening temperature, and chemical durability of the glass component, 2.0-3.0 wt % $ZrO_2$, and 1-4 wt % colorant.

An exemplary embodiment of the present invention provides a lithium disilicate glass-ceramic having a cristobalite crystal phase, the lithium disilicate glass-ceramic including a glass component including 11-13 wt % $Li_2O$, 70.0-77.0 wt % $SiO_2$, 2-3 wt % $P_2O_5$ as a nuclei formation agent, 2-5 wt % $Al_2O_3$ to increase glass transition temperature, softening temperature, and chemical durability of the glass component, 2.0-3.0 wt % $ZrO_2$, and 1-4 wt % colorant.

An exemplary embodiment of the present invention provides a method to manufacture a lithium disilicate crystalline glass component having a cristobalite crystal phase, the method including: a melting of a glass component, the glass component including 11-13 wt % $Li_2O$, 70.0-77.0 wt % $SiO_2$, 2-3 wt % $P_2O_5$ as a nuclei formation agent, 2-5 wt % $Al_2O_3$ to increase glass transition temperature, softening temperature, and chemical durability of the glass component, 2.0-3.0 wt % $ZrO_2$, and 1-4 wt % colorant; a first heat treatment to form a nuclei at 350-400° C. for 1-120 minutes; and a second heat treatment for a crystal growth at 550-690° C. for 1-120 minutes.

An exemplary embodiment of the present invention provides a prosthetic restoration material for single-tooth crowns and bridges, including a lithium silicate glass composition, the lithium silicate glass composition including a glass component including 11-13 wt % $Li_2O$, 70.0-77.0 wt % $SiO_2$, 2-3 wt % $P_2O_5$ as a nuclei formation agent, 2-5 wt % $Al_2O_3$ to increase glass transition temperature, softening temperature, and chemical durability of the glass component, 2.0-3.0 wt % $ZrO_2$, and 1-4 wt % colorant.

An exemplary embodiment of the present invention provides a prosthetic restoration material for single-tooth crowns and bridges, including a lithium disilicate glass-ceramic, the lithium disilicate glass-ceramic including a glass component including 11-13 wt % $Li_2O$, 70.0-77.0 wt % $SiO_2$, 2-3 wt % $P_2O_5$ as a nuclei formation agent, 2-5 wt % $Al_2O_3$ to increase glass transition temperature, softening temperature, and chemical durability of the glass component, 2.0-3.0 wt % $ZrO_2$, and 1-4 wt % colorant.

An exemplary embodiment of the present invention provides a method of forming cristobalite crystal phase and lithium disilicate crystal phase at the same time in the glass made from $Li_2O$—$Al_2O_3$—$SiO_2$—$Li_2O$—$K_2O$—$Na_2O$—$ZrO_2$—$CaO$—$P_2O_5$-coloring agents.

The applicable glass which enhances the strength and aesthetic light transmittance may include of 11-13 wt % $Li_2O$, 70-77 wt % $SiO_2$, 2-3 wt % $P_2O_5$ as a nuclei formation agent, 2-5 wt % $Al_2O_3$ to increase glass transition temperature, softening temperature, and chemical durability of the glass, 2-3 wt % $ZrO_2$, 0.5-3 wt % CaO for enhancing thermal expansion coefficient, 0.5-3 wt % $Na_2O$, 0.5-2 wt % $K_2O$, 1-4 wt % for other coloring agents (colorants). The glass may not contain MgO, ZnO, F, $La_2O_3$ because they reduce light transmittance.

The production of this amorphous or crystalline glass includes the nuclei formation or crystal growth processes, and one or two-stage heat treatment process to prevent or reduce the progress of cracking by increasing the size of cristobalite crystals inside the glass. This process forms crystal phases with the nuclei formation heat treatment (the first stage) at 350-400° C. for 1 to 120 minutes, followed by the other heat treatment (the second stage) at 550-690° C. for 5 to 120 minutes.

These amorphous of crystalline glasses are processed into the prosthetic shapes with computer-aided design and computer-aided manufacturing (CAD/CAM) method after the materials undergo the first and second stage processes, which show increased strength after the additional third heat treatment at 690-750° C. for 5 to 120 minutes.

The prosthetic shapes can be pressure-cast with the amorphous or crystalline glass with and without the first two heat treatments. The pressure-casting heat treatment is done in a separate dental pressure-casting facilities and vacuum equipment at 890-950° C. for 5 to 120 minutes.

It is to be understood that both forgoing general descriptions and the following detailed description are exemplary and explanatory and are intended to provide further explanation of the invention as claimed. Other features and aspects will be apparent from the following detailed description, the drawings, and the claims.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
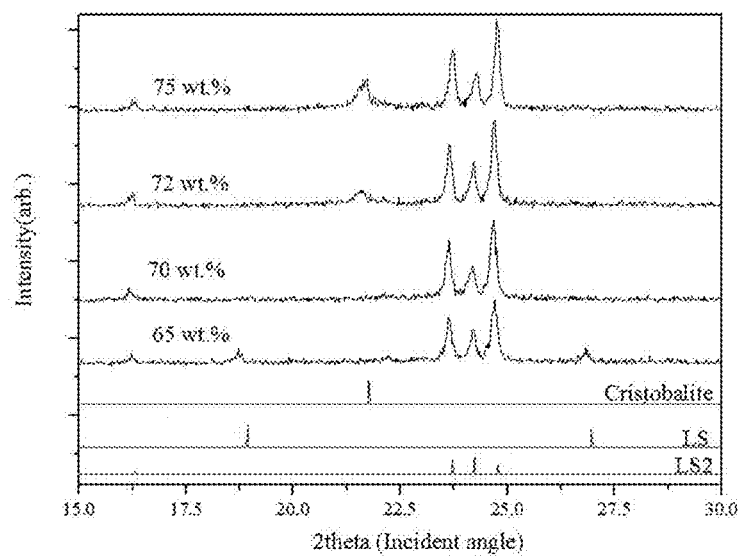
FIG. 1 illustrates X-ray diffraction results on the sample powdered after the final heat treatment according to an exemplary embodiment of the present invention.

Exemplary embodiments of the present invention will be described more fully hereinafter with reference to the accompanying drawings. However this exemplary embodiment is provided to enhance the sufficient understanding of those who possess the common knowledge in this field, thus it can be modified to various forms, and the scope of present invention is not limited to the following exemplary embodiment.

High strength crystalline glass for dentistry proposed by an exemplary embodiment of the present invention contains amorphous and crystalline lithium disilicate. Since its overall color is very similar to teeth, its high aesthetic traits are suitable for dental materials.

The aesthetic traits, especially light transmittance, are affected largely by the degree of light scattering resulting from the refractive index difference between different crystal phases in dense bulk. The refractive index of cristobalite is 1.48. The increased content of cristobalite increases the interfaces with the mother glass or lithium disilicate crystal phase, which leads to decrease in low light transmittance due to increased light scattering. Therefore, only the controlled amount of cristobalite crystal phase may need to be formed in the glass to show adequate light transmittance for dental purpose.

The strength of the crystalline glass may be improved with a compressive stress formed between different phases with different thermal expansion coefficients. The thermal expansion coefficient of cristobalite is $10.9 \times 10^{-6}$/° C. (Marcus P. Borom, Journal of The American Ceramic Society, vol. 58, no. 9-10, 1975) Therefore, the design of glass component is important for the glass to have lower thermal expansion coefficient than that of cristobalite to induce a compressive stress inside of the mother glass.

Further, the lithium disilicate glass-ceramics containing cristobalite crystal in this above exemplary embodiment of the present invention has higher biaxial flexural strength than that of previously proposed lithium disilicate crystalline based glasses (approximately 350 MPa), and is applicable as a prosthetic material for aesthetic purposes considering high light transmittance. These amorphous glass or crystalline glass are applicable to monolithic crowns and bridges, which are bound to the top surface of zirconia when used for high strength prosthetic materials. This embodies strength and aesthetic traits, allowing the application to posterior or bridges exposed to high strength. The bond strength at zirconia-lithium disilicate crystalline glass-ceramics interface manufactured with this exemplary embodiment of the present invention showed twice the tensile bond strength of porcelain-fused-to-metal (PFM).

The followings explain examples of the method to manufacture dental glass or lithium disilicate crystalline glass containing cristobalite.

The high strength dental glass presented in this embodiment are crystalline glass containing lithium disilicate crystal, cristobalite, lithium phosphate crystal, which also contains 11-13 wt % $Li_2O$ and 70-77 wt % $SiO_2$ as main components of the crystalline glass, 2-3 wt % $P_2O_5$ working as nuclei formation agent, 2-5 wt % $Al_2O_3$ to increase glass transition temperature and softening temperature as well as chemical durability of the glass, 2-3 wt % $ZrO_2$, 0.5-3 wt % CaO for enhancing thermal expansion coefficient, 0.5-3 wt % $Na_2O$, 0.5-2 wt % $K_2O$, 1-4 wt % for other coloring agents (colorants), and not containing MgO, ZnO, F, $La_2O_3$ because they reduce light transmittance.

The alkali oxide may be one of $K_2O$ and $Na_2O$ or include both $K_2O$ and $Na_2O$.

The optimal weight ratio of $SiO_2$ and $Li_2O$ ($SiO_2$ content/$Li_2O$ content) is desired to be 2:1 to 10:1 considering the composition of lithium disilicate crystal in the crystalline glass.

Further, the high strength dental crystalline glass from the exemplary embodiment may not contain MgO, ZnO, $La_2O_3$ to maintain light transmittance needed for dentistry purpose.

The recommended $ZrO_2$ content is 2-3 wt %, at which level opacity increase after the crystallization heat treatment, because the aforementioned components promote the crystal growth resulting in increased content of crystal phases in the crystalline glass. $ZrO_2$ content less than 2 wt % leads to speckles or opaque crystalline glass, while its content more than 3 wt % increases a flow of the glass resulting in deformation after crystallization heat treatment, and increases in yellow intrinsic to $ZrO_2$ which makes difficult the manufacture into products.

Further, the high strength dental crystalline glass from the exemplary embodiment may contain additional 1-4 wt % coloring agent to provide the same or similar color with teeth. The coloring agent is to provide the same, similar, and fluorescent colors, including red iron oxide ($Fe_2O_3$), ceria ($CeO_2$) for yellow, vanadium (V) oxide ($V_2O_5$) for orange, $V_2O_3$, $Er_2O_3$, $Tb_2O_3$, $Pr_2O_3$, $TaO_2$, $MnO_2$ or their mixture for black. For example, red iron oxide ($Fe_2O_3$), ceria ($CeO_2$), or vanadium (V) oxide ($V_2O_5$) is mixed with starting materials, which provides light yellow similar to teeth during melting, while $TiO_2$ show white very similar to teeth color.

$Li_2CO_3$ instead of $Li_2O$ may be added when the aforementioned starting materials are weighed and mixed. Carbon dioxide ($CO_2$) from carbon component of $Li_2CO_3$ escapes as gas during glass melting process. For alkali oxide, $K_2CO_3$ and/or $Na_2CO_3$ instead of $K_2O$ and $Na_2O$ may be added, and carbon dioxide ($CO_2$) from carbon component of $K_2CO_3$ and/or $Na_2CO_3$ escapes as gas during a glass melting process.

The mixing process employs dry mixing processes, one of which is ball milling. The starting materials are introduced to a ball milling machine, which rotates at a constant speed to mechanically grind and mix uniformly. The balls for milling may be ceramic including zirconia and/or alumina, and they may have a uniform or two different sizes. The size of balls, milling duration, and rotation per minute (rpm) are controlled according to the desired size of particles. For example, considering particles size, the size of balls may be around 1-30 mm, angular speed of the ball milling machine may be set to 50-500 rpm. It is desired to run the machine for 1 to 48 hours depending on particles size. The starting material turns into fine particles with uniform size, mixed uniformly.

The starting materials are melted in a melting furnace after they are placed in it. Melting means the phase transition of the starting materials from solid to liquid with viscosity. Because it requires high melting point, high strength, and high contact angle to prevent the starting materials from being stuck on the furnace surface, the melting furnace made from materials like platinum, diamond-like-carbon (DLC), or chamotte, or the one coated with platinum or DLC is highly recommended.

The recommended melting conditions are 1400-2000° C. for 1 to 12 hours at an atmospheric pressure. Since the starting materials may not melt under 1400° C., and the process demands an unnecessary high energy input above 2000° C., the recommended temperature range should be kept. Too short melting time is not advised due to possibly insufficient melting, while too long melting time is not advised due to excessive energy consumption, making the process uneconomical. The temperature ramping rate is recommended to be 5-50° C./min. Because too slow a rate decreases the productivity due to long processing time, and too high a rate increases volatility resulting in poor crystalline glass properties, the aforementioned ramping rate is highly recommended. Oxidizing environments, such as oxygen or air atmosphere, are recommended.

Melted material is poured onto specific die molds to obtain dental crystalline glass with desired shapes and sizes. High melting point, high strength, and high contact angle to prevent it from being stuck on surfaces may be required for the materials for these die molds. Graphite and carbon are such materials, which need preheat to 200-300° C. before pouring melted materials into die molds to prevent or reduce heat shock.

After the melting materials in the molds cool down to 60-100° C., nuclei formation and crystal growth of glass are implemented after being transferred to heat treatment incinerator. The conditions for nuclei formation and crystal growth are recommended at 350-400° C. for 1-120 minutes at an atmospheric pressure. The fast nuclei formation leads to amorphous phase. The nuclei formation is difficult with the heat treatment below 350° C. since it does not induce thermal vibration, while the process above 400° C. is not recommended due to possible increase in the size of the nuclei, poor material properties, and low energy efficiency. The crystal growth is recommended to perform at 550-690° C. for 5 to 120 minutes, the resulting main crystal phase for this process being lithium disilicate. The excessive crystallization occurring at above 690° C. makes CAD/CAM processing difficult. CAD/CAM processing may be implemented after the heat treatment for nuclei formation, or after nuclei formation and crystal growth process. The final heat treatment is recommended at 690-750° C. for 5 to 120 minutes. The strength of the cristobalite crystal phase and lithium disilicate crystal phase increases due to compressive stress caused by thermal expansion coefficient difference in mother glass. Crystal phases melt to amorphous phase above 750° C., which may lead to collapse in shapes.

Insufficient heat treatment duration may result in insufficient crystal growth, and extended heat treatment duration may not be economical due to excessive energy consumption. The temperature ramping rate toward the heat treatment temperature is recommended at 10-60° C./min. Because too slow a rate decreases the productivity due to long processing time, and too high a rate increases volatility resulting in poor crystalline glass properties, the aforementioned ramping rate is highly recommended. Oxidizing environments, such as oxygen or air atmosphere, are recommended. The heat treatment causes the movement of atoms in glass structure which leads to phase transition of the glass. Crystalline glass can be obtained from crystallization, which includes lithium disilicate crystal as main phase caused by a crystal growth from heat treatment.

The crystal phases and the composition thereof may vary according to heat treatment temperature. The crystals, such as lithium disilicate ($Li_2Si_2O_5$), lithium phosphate ($Li_3PO_4$), and cristobalite (SiO2), grow according to heat treatment temperature, and the crystal phases and the composition thereof may also vary by the components of the starting materials and their compositions.

The block obtained from aforementioned crystalizing heat treatment is made into crown shapes through pressure-casting and cutting, or may be placed directly on zirconia substructures with pressurized casting process.

The pressure-casting process decreases the viscosity of amorphous or crystalline glass ingot at 850-980° C., followed by pressing it into an empty space in a form of a crown located inside of the investment. At the same time, the amorphous phase transits into lithium disilicate crystal phase. The lithium disilicate ingot itself becomes lithium disilicate crystal phase after pressure-casting and heat treatment, showing difference by having uniaxial crystal phase increase. After the amorphous or lithium disilicate crystalline block is cut into crown shapes with CAD/CAM equipment, heat treatment at 690-750° C. produces crystalline glass crown of cristobalite, lithium disilicate crystals.

The crown-shaped lithium disilicate crystalline glass from aforementioned processes is bound to a zirconia substructure, which utilizes cementation and heat-treated joining from binding agent to place lithium disilicate crystalline glass on the zirconia substructure. Cementation uses existing photosynthetic binding agents. Heat-treated joining is more suitable for high binding strength and the stability of the binding interface. This method uses inorganic binding agents including complex metal oxides, which undergoes heat treatment at 720-850° C. for 1-120 minutes and binds the crystalline glass to a zirconia substructure. Temperature under 720° C. decreases binding strength, while temperature over 850° C. may deform the crystalline glass in crown shapes.

Lithium silicate amorphous or crystalline glass may be directly placed on a zirconia substructure with pressure-casting. One or more zirconia substructures may be placed in an investment, then the space for glass materials may be made with the lost wax method. Though lithium silicate amorphous or crystalline glass can be cast at high pressure directly on the top surfaces of zirconia, coating the binding agent first on the zirconia substructures is recommended by heat treating at 750-1000° C. to increase the binding strength, followed by pressurized casting to place lithium silicate amorphous or crystalline glass. The binding agent not only increases the binding strength, but also enhances wettability of the glass. The inorganic binding agent does not melt under 750° C., while temperature over 1000° C. causes surface tension due to low viscosity, resulting in uneven covering of zirconia surface.

The manufacturing process of using amorphous lithium silicate ingot glass without crystallization heat treatment is described hereafter.

An amorphous block ingot is produced by first quenching melted materials previously heated to 1400-2000° C., then preparing glass powder by grinding quenched glass to increase the homogeneity of the glass, and finally shaping the glass by pouring it into the molds following reheat of glass powder to 1400-2000° C.

The amorphous block ingot requires an annealing process for cutting and shaping, followed by a heat treatment at 350-400° C. for 1 to 120 minutes to reduce the stress from quenching. The block ingot from this process may be directly placed on the top surfaces of zirconia in the pressurized cast process, or placed on the zirconia coated with the binding agent as described earlier. Through the processes described above, the high strength crystalline glass or crystalline glass pressed on zirconia may be used to selectively manufacture artificial teeth such as veneer, posterior, bridge, and the like.

An exemplary embodiment of the present invention provides a method of forming cristobalite crystal phase and lithium disilicate crystal phase at the same time in the glass made from $Li_2O$—$Al_2O_3$—$SiO_2$—$Li_2O$—$K_2O$—$Na_2O$—$ZrO_2$—$CaO$—$P_2O_5$-coloring agents. The experimental results show that the thermal expansion coefficient and strength as functions of $SiO_2$, $Na_2O$, $K_2O$ compositions, and the components that control the thermal expansion coefficient of the glass.

Figure 2:
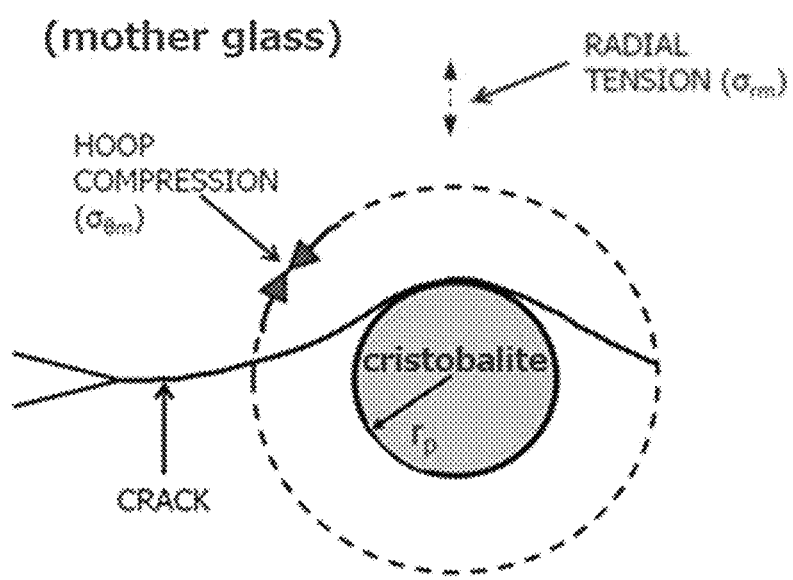
FIG. 2 illustrates strength-increasing mechanism of the lithium disilicate glass-ceramics containing cristobalite crystal phases according to an exemplary embodiment of the present invention.
Figure 3:
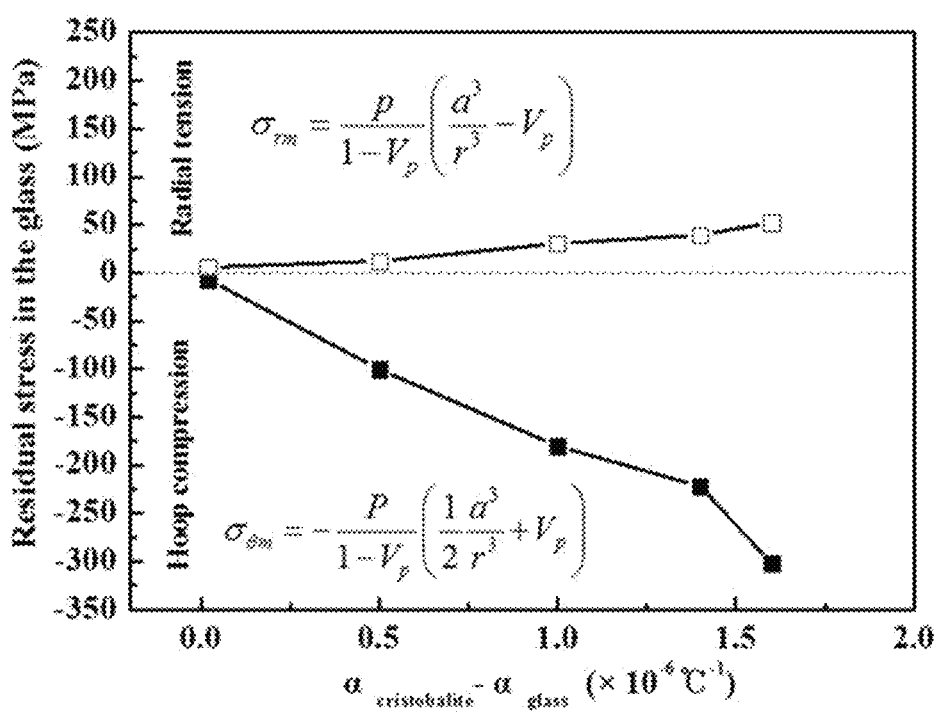
FIG. 3 illustrates a calculation result for the residual stress in the crystalline glass according to an exemplary embodiment of the present invention.

The glass after the final heat treatment in this embodiment starts to form cristobalite crystal phases inside the glasses with over 70 wt % $SiO_2$, which provides the strength increase effect from the increase in compressive stress as shown in FIG. 2 and FIG. 3, caused by low thermal expansion coefficient of the processed glass compared to that of cristobalite crystal phase. As shown in FIG. 3, the higher difference between thermal expansion coefficient of the glass and that of cristobalite crystal phase leads to higher compressive stress, which results in the strength enhancement. However, the $SiO_2$ content higher than 77 wt % brings about too large difference between thermal expansion coefficients, which causes microcracks resulting in strength decrease.

Since the addition of $SiO_2$ more than 77 wt % forms excessive cristobalite crystal phases, of which interfaces with lithium disilicate scatters light to decrease aesthetic traits, less than 30 wt % cristobalite crystal phases are recommended for the best aesthetic properties.

Figures 4, 5:
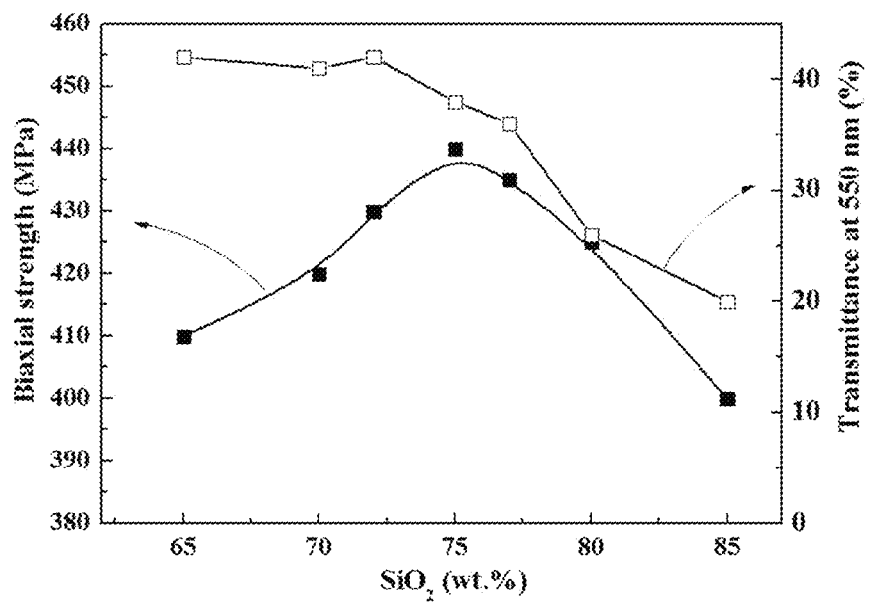
FIG. 4 describes a biaxial flexural strength and light transmittance after the final heat treatment of the crystalline glass according to an exemplary embodiment of the present invention.
FIG. 5 illustrates a thermal expansion coefficient of the glass according to an exemplary embodiment of the present invention.

Therefore, the amorphous or crystalline glass according to an exemplary embodiment of the present invention contains $Li_2O$—$Al_2O_3$—$SiO_2$—$Li_2O$—$K_2O$—$Na_2O$—$ZrO_2$—$CaO$—$P_2O_5$-colorants with the high applicability as aesthetic and strong prosthetic materials of which composition is 70-77 wt % $SiO_2$ as shown in FIG. 4. The glass also requires the thermal expansion coefficient of $9.5-9.9\times10^{-6}/°$ C. to match that of zirconia for further binding with zirconia. As shown in FIG. 5, the amorphous or crystalline glass with 72-75 wt % $SiO_2$ has the thermal expansion coefficient suitable for binding to zirconia, which increases the joining bind strength by two to three times. This amorphous or crystalline glass may be applied to monolithic crowns or glass-ceramics pressed on zirconia crowns, and especially to bridges requiring high mechanical strength.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A lithium disilicate glass-ceramic having a crystobalite crystal phase, the lithium disilicate glass-ceramic comprising:
    a glass component comprising 11-13 wt % $Li_2O$, 70.0-77.0 wt % $SiO_2$, 2-3 wt % $P_2O_5$ as a nuclei formation went 2-5 wt % $Al_2O_3$ to increase glass transition temperature, softening temperature, and chemical durability of the glass component 2.0-3.0 wt % $ZrO_2$, and 1-4 wt % colorant.

2. The lithium disilicate glass-ceramic of claim 1, further comprising 1-5 wt % $K_2O$ and/or $Na_2O$, and 0.5-3 wt % CaO.

3. The lithium disilicate glass-ceramic of claim 2, wherein the lithium disilicate glass-ceramic comprises 0.5-2 wt % $K_2O$.

4. The lithium disilicate glass-ceramic of claim 1, wherein an amount of the $SiO_2$ is in a range of 72.0-75.0 wt %, and wherein the glass component has a thermal expansion coefficient in a range of $9.5-9.9\times10^{-6}/°$ C. in 100-400° C. range.

5. The lithium disilicate glass-ceramic of claim 1, wherein the glass component comprises the 2.0-3.0 wt % $ZrO_2$, without including MgO, ZnO, F, and $La_2O_3$.

6. A method to manufacture a lithium disilicate crystalline glass component having a cristobalite crystal phase, the method comprising:
    melting of a glass component comprising 11-13 wt % $Li_2O$, 70.0-77.0 wt % $SiO_2$, 2-3 wt % $P_2O_5$ as a nuclei formation agent, 2-5 wt % $Al_2O_3$ to increase glass transition temperature, softening temperature, and chemical durability of the glass component, 2.0-3.0 wt % $ZrO_2$, and 1-4 wt % colorant;
    performing a first heat treatment to form a nuclei at 350-400° C. for 1-120 minutes; and
    performing a second heat treatment for a crystal growth at 550-690° C. for 1-120 minutes.

7. The method of claim 6, further comprising:
performing a nuclei formation process forming a nuclei in an amorphous phase after the first heat treatment; and
performing a nuclei growth process forming a lithium disilicate crystal phase as a main phase using the nuclei formed after the second heat treatment.

8. The method of claim 6, further comprising:
performing a pressure-casting process which pushes a glass component formed after the first heat treatment process, or a lithium disilicate crystalline glass component formed after the first and second processes, into a crown-shaped void at 890-950° C.; or
performing a machining of the glass component formed after the first heat treatment process, or the lithium disilicate crystalline glass component formed after the first and second processes, into a crown shape with CAD/CAM equipment, followed by a third heat treatment at 690-750° C.

9. The method of claim 6, further comprising:
binding, using a binding agent, a glass component formed after the first heat treatment process or a lithium disilicate crystalline glass component formed after the first and second processes to a zirconia substructure at 890-950° C.,
wherein the binding agent is heat-treated at 750-1000° C. for 1-120 minutes.

10. A prosthetic restoration material for single-tooth crowns and bridges, comprising the lithium disilicate glass-ceramic of claim 1.

* * * * *